Figure 3:
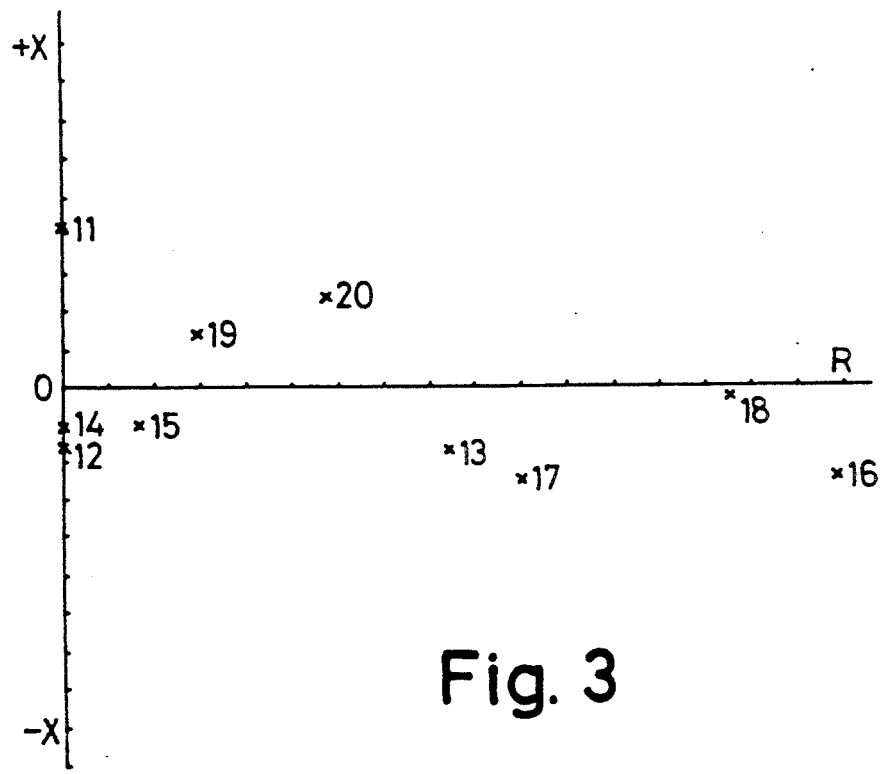

United States Patent [19]
Mayo

[11] Patent Number: 5,189,366
[45] Date of Patent: Feb. 23, 1993

[54] METHOD AND APPARATUS USING A VARYING ELECTROMAGNETIC FIELD FOR DETERMINING THE NATURE, OR A PROPERTY OF A NON-METALLIC MATERIAL

[75] Inventor: Geoffrey Mayo, Warsash, United Kingdom

[73] Assignee: Loma Group Limited, United Kingdom

[21] Appl. No.: 454,731

[22] Filed: Dec. 18, 1989

[30] Foreign Application Priority Data

Dec. 20, 1988 [GB] United Kingdom ................ 8829617

[51] Int. Cl.$^5$ ..................... G01N 27/72; G01R 33/12
[52] U.S. Cl. ................................. 324/233; 324/225; 324/239
[58] Field of Search ............... 324/225, 233, 234, 236, 324/239, 71.1, 240, 241, 242, 243

[56] References Cited

U.S. PATENT DOCUMENTS

| | | | |
|---|---|---|---|
| 2,477,057 | 7/1949 | Grady, Jr. | 324/239 |
| 2,587,664 | 3/1952 | Stout | 324/243 |
| 3,665,302 | 5/1972 | Lees et al. | 324/64 |
| 4,553,094 | 11/1965 | Gehrke | 324/225 |

FOREIGN PATENT DOCUMENTS

WO88/03273  5/1988  PCT Int'l Appl. ................ 324/239

OTHER PUBLICATIONS

Discriminating Method for Freshness, Ripeness, Internal Quality of Vegetable and Fruit, H. Kato, Patent Abstract of Japan, vol. 12, No. 210, p. 717, (3057) Jan. 1988.

Primary Examiner—Walter E. Snow
Attorney, Agent, or Firm—Silverman, Cass & Singer, Ltd.

[57] ABSTRACT

Method and apparatus for determining the nature or property of a non-metallic material in which the material is passed through a time varying magnetic field. The signals which are induced in the sensing coil for the magnetic field are processed for measurement. Although the material is non-metallic, it may have sufficient conductivity at the frequencies employed to cause the flow of eddy-currents to generate a measurable signal. The method of the invention also provides for measurement of permittivity or diamagnetic properties of the material which may also give rise to small measurable signals.

21 Claims, 4 Drawing Sheets

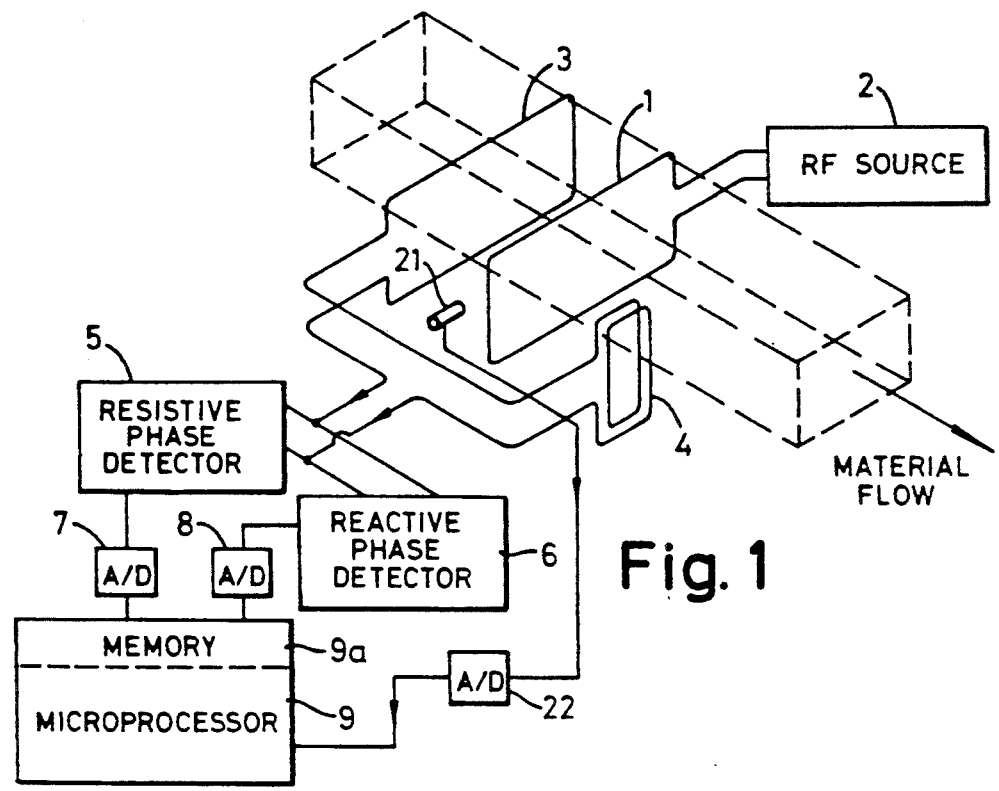
Fig. 1
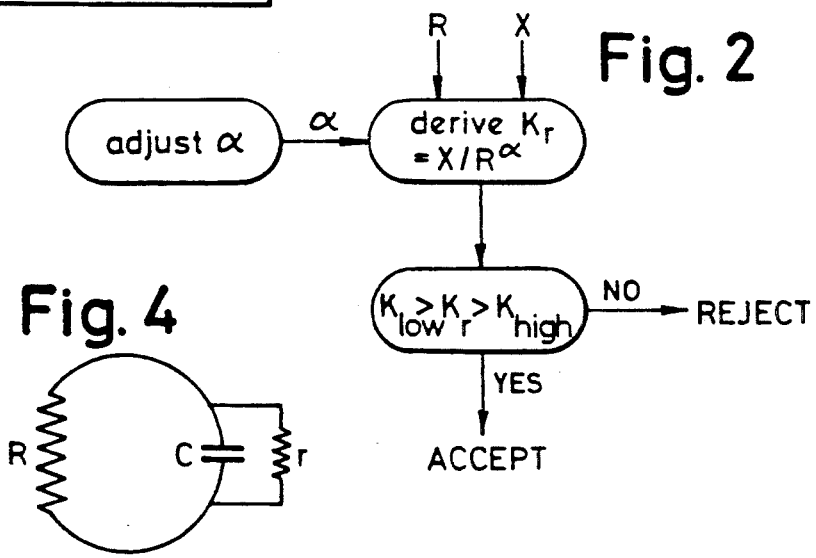
Fig. 2
Fig. 4
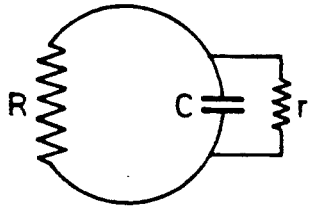

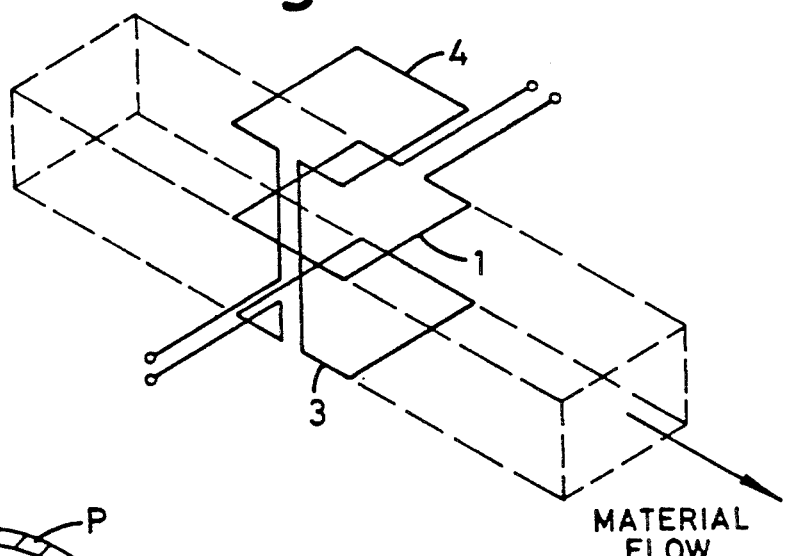
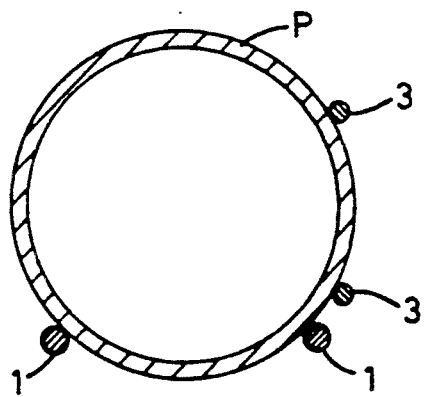

METHOD AND APPARATUS USING A VARYING ELECTROMAGNETIC FIELD FOR DETERMINING THE NATURE, OR A PROPERTY OF A NON-METALLIC MATERIAL

This invention relates to a technique for determining the nature or a property of a non-metallic material. The technique involves passing the material through a time varying magnetic field and processing the signals which are induced in a sensing coil. Although the material is non-metallic, it may have sufficient conductivity at the frequencies employed to cause e.g. the flow of eddy-currents which generate a signal. The material will also possess permittivity or diamagnetic properties which may also give rise to small signals which are measurable by a method in accordance with the invention.

Applications of the invention include the identification or classification of food; determining the moisture/salt/ sugar content or the ripeness/freshness or maturity of food; the air content and/or degree of freezing of ice cream; controlling an iron additive; measuring bulk or core temperature of a material whose conductivity is temperature dependent and determining the fat/lean/bone ratio of meat.

Whilst reference is made herein to techniques involving the nature or a property of food, it will be understood that the invention is not limited to use in the food industry.

GB-A-1398735 discloses a method and apparatus for measuring fat content in animal tissue. The reference recognises that the majority of body cells contain electrolyte while fat does not, hence fat has a much lower electrical conductivity than lean meat. It also teaches that, at very high frequencies, in the range of from 10 MHZ-100 GHZ, lean conducts more than fat and that at 10 MHZ in particular, lean conducts approximately twenty times as much as fat. The reference compares and contrasts "capacitative or direct coupling", "radiative coupling" and "inductive coupling" but specifically teaches the use of inductive coupling involving the use of an electromagnetic field of known intensity. The technique includes introducing a sample into the field (where it remains or is held captive) and measuring the effect of the sample on the field. Generally, the sample is placed on the axis of a long coil which is carefully shielded to guard against extraneous influences. The coil is energised with a high frequency signal (of the order of 10 MHZ) and a sensing coil is used in a feedback system to control a variable gain circuit coupled to a power amplifier whereby the field is maintained at a substantially constant value. Currents induced in the sample cause energy to be lost in the form of Joule heating. This loss, in addition to the electrical inertia effect of the induced currents, is reflected back into the coil system as a change in load or driving impedance. This load impedance change is sensed so as to provide a measure of power absorption and the amount of power absorbed is related to a fat/lean content with respect to the body weight of the sample.

The reference specifically teaches (equation 1) that a good approximation can be made for the influence of the real part of the load impedance on power absorption. More specifically the power (P) induced in a sample is related to its dimensions and physical properties and to the square of the frequency ($\omega^2$). In particular the power (P) induced in the sample (i.e. equation 1) can be determined under conditions where the reactance has a value which is a second order lower than the resistance and hence the reactance can be ignored. Such conditions involve the use of very high frequencies (in the MHZ range) which effectively obviate the reactance effect. In other words, the resistive effect increases in accordance with $\omega^2$, whereas the reactive effect is only proportional to $\omega$.

Since this prior art technique employs very high frequencies (e.g. 10 MHZ), it would be impossible to detect a change in the reactive component of a signal induced in the sensing coil (i.e. due to the sample) because it si so small as to be swamped by the resistive signal. The reference therefore neither addresses, nor teaches the use of sensitive detectors for measuring reactive components. However, as will become apparent below, the present invention depends on measuring the changes in both reactive and resistive components since it employs a technique which not only operates at, for example, frequencies which are about two orders of magnitude lower than the frequencies used in the reference, but it also employs a detection technique which is, for example, two orders higher in sensitivity. Thus, compared with GB-A-1398735, the invention does not depend on measuring power absorption (since there is effectively no change in power during the course of measurement).

The invention also uses a dynamic technique, as will be explained below, in that the sample is passed through a special coil system so that a measurable change in a reactive component takes place as a result of a change in coupling. In GB-A-1398735, the technique is static because the sample is stationary in the coil system, and the technique depends on the difference between the measuring load impedance first with the coil "empty" and then with the coil "occupied" by the sample.

Whilst GB-A-1398735 describes a technique for determining fat/lean ratio in meat, it does not address any further areas of interest to the food industry. However, fruit and vegetables are a more important source of food (including products made by processing naturally occurring fruits and vegetables). Whilst health risks due to decay of fruits and vegetables may not be as severe as those encountered in the meat industry, it is highly desirable to determine their quality in view of their of fitness for consumption and their marketing. There have been no significant and practical proposals prior to the invention, for dealing with this problem.

GB-A-1603578 discloses a technique for distinguishing between various metallic objects. In particular, it teaches the use of a coil assembly to which a plurality of frequencies are applied in turn so as to provide a magnetic field for each frequency. Samples of the same metal but having different cross-sectional areas are introduced to the coil assembly. The true resistive component of voltage unbalance due to each metallic sample is then measured. Phase shift compensation is essential so as to relate the true resistive component to a zero degree phase shift (i.e. within 1° of the phase of the applied frequency). An embodiment is also described in which two matched secondary coils are connected in bucking relationship and a variable resistor is connected to the secondary coil arrangement. Whilst the reference deals mainly with metal detection, it briefly mentions increasing the frequency to the 1-10 MHZ range to obtain a test result for conductive animal tissue.

Besides the fact that this references does not address the kind of problems which exist with testing the quality of foodstuffs, it also depends primarily on measuring a true resistive component and is hence distinct from the present invention.

Therefore, the overall problem facing the invention is to provide a general technique which can be used for determining the nature or a property of a non-metallic material, particularly a food, and which is flexible enough to be applied to different materials in order to provide accurate and reliable results.

In accordance with the invention, a method of determining the nature or property of a non-metallic material comprises the steps of:

(a) generating a time-varying electromagnetic field in a primary coil, (b) providing a sensing coil, in the vicinity of the electromagnetic field, (c) introducing the non-magnetic material into the field whereby a signal is developed in the sensing coil, and (d) detecting the signal developed in the sensing coil and using it to determine the nature or property of said material, the method being characterised by:

(e) using a frequency for generating said field which will provide a distinguishable change in the reactive component in the signal induced in the sensing coil due to the presence of said material in said electromagnetic field, (f) obviating any voltage induced in the sensing coil, due to said electromagnetic field alone, thereby to improve the sensitivity of the system for detecting said change in the reactive component, (g) determining resistive and reactive components of the signal induced in the sensing coil due to the complex impedance of the material as the material is passed through said field, and (h) using said components of the complex impedance to determine the nature or a property of the non-metallic material.

The resistive and reactive components may be determined as quadrature components, i.e. separated in phase by 90°, so that they may be mapped, for example, as points on an Argand diagram. On such a diagram, one axis represents true resistance and the other axis represents a true reactance, the position of the point corresponding with the coordinates of the true resistive and reactive components. Equally well, the resistive and reactive components may be represented by amplitude and the phase measurements which, as known to those skilled in the art, are equivalent parameters. Alternative polar or cartesian co-ordinate systems may be used, or anything equivalent thereto which will provide the same complex impedance information. Such alternatives are covered by the phrase "reactive and resistive components" as used herein, even where each component may include, for example, both a reactive and a resistive part. The essential requirement is that the complex impedance can be mapped as loci of points (depending on frequency) onto a co-ordinate system or otherwise similarly represented.

The components of complex impedance may be sensed by separate phase detectors operating at a relative phase difference of 90°. (However, the components could also be sensed with a different relative phase difference from which a definitive pair of co-ordinates may be derived.) Phase detectors operating on quadrature components enable purely reactive and purely resistive components to be readily determined. (However, phase detectors may also be used which produce signals that are each due to both reactive and resistive components from which the reactive and resistive components (or amplitude and phase) can be determined.)

Suitably, the frequency used for generating the varying electromagnetic field is in the range of 50 KHZ-1 MHZ but the frequency used will depend on the size and characteristics of the non-metallic material whose nature or property is to be determined. Usually, the frequency will be in the KHZ range in order to produce a distinguishable reactive effect (i.e. not swamped by the resistive effect).

Since the sensing coil is in the vicinity of the primary coil, it will usually have a massive voltage induced therein as a result of direct coupling. This voltage must be obviated because the changes in coupling due to passing the non-magnetic material through the field are infinitesimally smaller (e.g. the invention may have a sensitivity of 1 part in a million to sense the latter changes).

By using a system in accordance with the invention, where any voltage induced in the sensing coil is obviated, the sensitivity of detection is increased and very small changes of coupling due to the passage of a sample through the field are detectable. This sensitivity enables the use of much lower frequencies than in the above mentioned prior art references. The resistive component is therefore thousands of times smaller than in the prior art and is of an order of magnitude similar to that of the reactive component in order to provide meaningful complex impedance values which can be mapped onto a co-ordinate system.

The direct coupling voltage can be obviated, in one case, by arranging the sensing coil so that the plane of its windings are perpendicular to the plane of the windings of the primary coil. This largely reduces the latter voltage and smaller effects can be tuned out. However, other coil configurations are possible where the direct coupling voltage is balanced by inducing an opposite voltage in the sensing coil, due to the field generated by the primary coil. In this case, the direct coupling voltage is offset due to balancing the secondary coil system. This may be achieved in practice by using a dummy coil in which the opposite voltage is generated, but which does not otherwise cooperate with the primary coil since it does not form part of the path, through the coil system, along which the non-magnetic material passes in order to generate the complex impedance signal in the sensing coil. These coil configurations will be explained in more detail below.

The Applicant has found that eddy-currents will flow at high frequencies in vegetable matter having a cellular structure. This is a surprising effect in that such matter would normally be regarded as a non-conductor especially if measurements were carried out with direct current. This conductivity, which takes place at the frequencies used herein, has been found to be due to capacitive elements formed within the cellular plant structure. FIG. 4 is a schematic equivalent circuit for modelling the capacitative and resistive effect of vegetable material, such as an avocado pear. The capacitative eddy-currents give rise to positive reactive components which were previously only associated with magnetic materials. FIG. 3 is a schematic Argand diagram where the axes of the graph represent quadrature reactive and resistive components. It can be seen from this graph that certain foods have positive reactive components located at distinctive positions.

In the case of a fruit, such as an avocado pear, the frequency used can be such that the reactive and resistive components are comparable and the phase difference is approximately 45°. This is advantageous in that the Applicant has also found that the phase angle between the reactive and resistive components changes as a fruit ripens (or deteriorates) and hence it is a measure of its freshness. Preferably, therefore a frequency is selected where the reactive component is comparable with the resistive component.

The invention therefore opens up a new field of food analysis, since it can be used in different ways either to check on the freshness or maturity of a variety of foods, or to control processes associated with their preparation, storage or handling.

In particular, the invention provides a method for determining the freshness or maturity of a food in which an eddy-current can be induced, or which possesses permittivity or diamagnetic properties, the method including the steps of:

(a) providing model values of complex impedance representing changes in the food with time, (b) generating an hf field with a frequency which produces a distinguishable change in the reactive component of voltage induced in the food when passed through said field, (c) obviating any voltage induced in a sensing coil due to said field only, which sensing coil is used to detect said reactive component and a resistive component, (d) measuring both the reactive and resistive components induced in the sensing coil due to the complex impedance of the food, and (e) correlating said components with said model values in order to provide an optimum correlation which is used to determine the freshness or maturity of the food.

In the case of vegetable matter, for example, a potato or an avocado pear, or a melon, the vegetable matter will have a measurable electrical conductivity depending not only on its basic composition, but also on its freshness. As such matter decays, changes take place at cell boundaries and these lead to an increase in the resistive component and a decrease in the capacitative component. These changes can be used to determine the degree of decay and the invention can therefore be applied e.g. for sorting fruit, or for determining its storage life, e.g. for labelling in marketing outlets, and for other purposes.

In the case of meat, the relative proportions of fat, lean and bone will effect its conductivity. Also the resistive component is more dominant and it can be used as a guide to the proportions of these constituents in a portion of meat. However, the invention can alternatively be used, for example, to determine the maturity of meat such as air dried salami. In this case, it has been found that from 5 days to 25 days old, conductivity readings dropped progressively to one half of the initial value and hence changes in the resistive components were found to be valuable as a measurement for monitoring the drying process and as an in-line check on a suitable degree of maturity for slicing.

The invention may be used to identify different foods passing through the coil system since different foods will provide different characteristic reactive and resistive components. The phase of the sensed signal is relative to the phase of the drive voltage which creates the electromagnetic field and the amplitude and phase of the sensed signal will depend on the frequency which is employed. Hence, knowing these characteristics, a food can be identified.

Certain foods may not exhibit both reactive and resistive components, for example, as in the case of perfect insulators like fats and oils. However, fats have a negative reactive component due to their diamagnetic permeability. Pure water also has only a reactive component due to its diamagnetic permeability ($\mu = 0.999991$) and, when pure, it does not conduct. The degree of accuracy required to detect such a value is 9 parts in a million but this can be achieved with the invention due to the sensitivity of sensing and measuring phase angle. Tap water contains sufficient mineral elements to show a considerable degree of conductivity and hence produces a stronger effect.

Fruits and vegetables have been found to exhibit a positive reactive effect, previously only associated with magnetic effects. This is due to their cellular nature where eddy-currents are enhanced (at the frequencies used herein) due to a capacitance formed at cell boundaries. Changes in the reactive component and in both the reactive and resistive components can represent a change in quality since ripening of vegetables and fruits cause changes in the cell structure leading to alterations in either, or both of these components. Only the sensitivity of the invention has shown these alterations to be measurable.

Thus, the invention can be used to provide a ready means of checking foods for freshness and quality without human intervention or handling. It can also be used without damaging foods that are checked and it can be used "online", i.e. where food is transported on a conveyor belt.

The reactive and resistive components may be converted into digital values and these values may then be compared with a range of digital values which represent acceptable or non-acceptable qualities for a particular kind of food. Alternatively, or in addition, a library of digital values may be stored for different foods so that different kinds of foods can be distinguished, e.g. by computing the best correlation in accordance with a computer program. Digital values may also be stored for comparison with test values to determine the relative proportions of, e.g. lean/fat/bone in meat. In all cases, the food can simply be passed through a sensing head of a system which includes suitable signal processing means and means for effecting certain operations such as rejecting undesirable items or assessing them for the purposes of stock control and so on.

According to one embodiment of the invention, the method is carried out with a sensing head comprising:

(a) first coil means for generating a time-varying electromagnetic field, (b) second coil means adjacent said first coil means and in which a voltage is induced due to said field only, said first and second coil means both encompassing a region through which a non-metallic material can be passed, and (c) third coil means adjacent said first coil means but not encompassing said region, said third coil means being dimensioned so that an opposite voltage is induced therein to substantially offset the voltage induced in said second coil means.

The above sensing head uses an axial field which induces eddy-currents in a vertical plane in the cross-section of the sample passed through the coil system. For flat products (such as hamburgers) a more effective eddy-current path would be within the horizontal plane and this requires a vertical field.

In the latter case, the sensing head comprises:

(a) first coil means for generating a time-varying electromagnetic field, (b) second coil means adjacent said first coil means in which a voltage is induced due to said field only, said first and second coil means being wound in parallel planes which are spaced apart to define a path through the sensing head for a non-magnetic material to be passed, and (c) third coil means also wound in a plane parallel to said first coil means but not cooperating therewith to define said path, said third coil means being dimensioned and positioned so that an opposite voltage is induced therein to substantially offset the voltage induced in said second coil means.

In some cases, the third coil means may be dispensed with by providing a sensing head comprising:

(a) first coil means for generating a time-varying electromagnetic field, (b) second coil means arranged adjacent said first coil means but having the plane of it windings perpendicular to the plane of the windings of said first coil means, and (c) means defining a path for non-magnetic material to be transported adjacent said first and said second coil means, said first and second coil means cooperating when the non-magnetic material is transported on said path whereby a signal is induced into said second coil means.

Any of the above sensing heads may be used in apparatus further comprising:

(a) means for energising said first coil means with a frequency which will provide a distinguishable change in the reactive component in the signal induced in said second coil means, (b) means for passing the material through said region or along said path, (c) means for sensing a signal in said second coil means due to the passage of the non-magnetic material, (d) means for determining reactive and resistive components of the signal, and (e) means responsive to the reactive and resistive components for identifying or determining a property of the non-metallic material.

The invention recognises a further problem in that the reactive and resistive components of the detected signal can be each affected differently by the size and orientation of the non-magnetic material passing through the field (depending on the direction of the field). For example, fruit can vary in size although it may have a generally constant shape and conductivity (e.g. as in the case of a melon). Alternatively, wedges of cheese may have the same general size and shape but they could pass through the field in different orientations. Thus, changes in the cross-section of the material passing through the field will cause changes in the reactive and resistive components due to the change in the relative phase angle between the sensed pulsating signal and the pulsating field. Whilst these changes can be compensated by inputting data relating to size and/or orientation, or by taking steps to size grade objects and (if necessary) to orientate them before sensing, this would be a laborious and/or expensive and time consuming operation.

The invention solves this further problem by indicating in the above method, the step of processing the reactive and resistive components and using the processed components to compute a value which is substantially unaffected by changes in the cross-section of the material passing through the electromagnetic field.

In a preferred embodiment of the invention, the reactive and resistive components are processed in accordance with the expression:

$$K_r = \frac{X}{R^a}$$

where R is the amplitude of the resistive component of the sensed signal, X is the amplitude of the reactive component of the sensed signal, $a$ is a power which is normally such that $0.5 \leq a \leq 1.0$ (depending on the geometry of the material relative to the coil, i.e. its shape and orientation), and $K_r$ is an amplitude which is computed. This amplitude $K_r$ will vary in accordance with changes in the conductivity of the material but it will be substantially independent of the cross-section of the material passing through the field in the detection zone.

The apparatus of the invention therefore preferably includes signal processing means for processing the purely reactive and resistive components and for computing a value which is substantially independent of the cross-section of the material passing through the electromagnetic field. More particularly, the processing means is programmed to manipulate digital values representing the reactive and resistive components, in accordance with the above expression in R, X and $a$ and to provide a signal based on $K_r$. Such a signal may be used in a variety of ways, i.e. to recognise a material, to check for quality, to reject unsatisfactory products or to control a process (e.g. for continuously producing a sausage-meat product in which the constituents may vary). In practice, significant variations are monitored and minor variations may be tuned out, or eliminated e.g. by applying a correlation technique.

Figure 5:
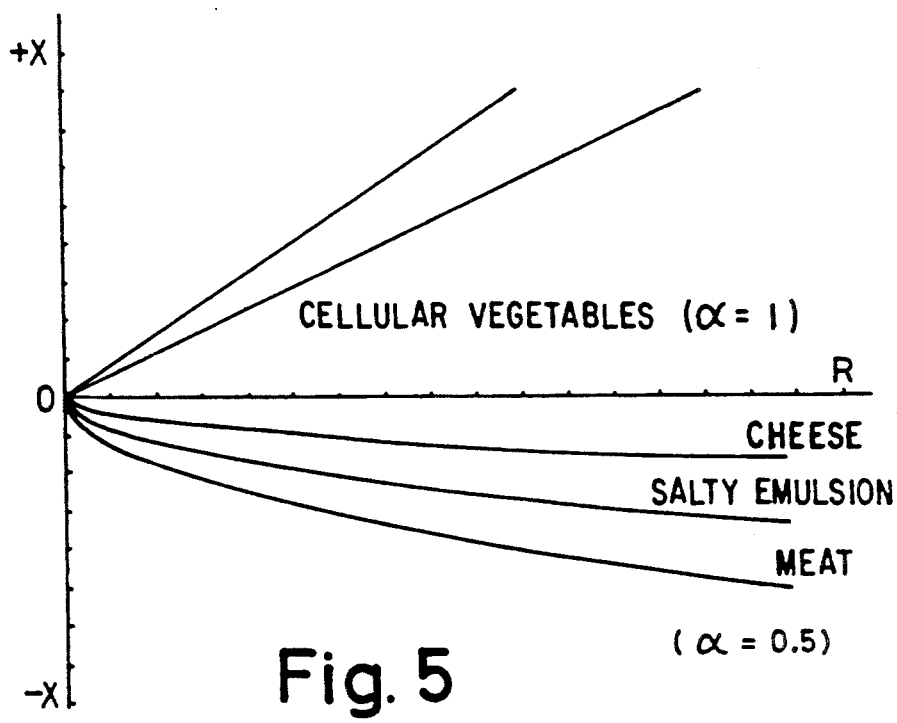
Figure 6:
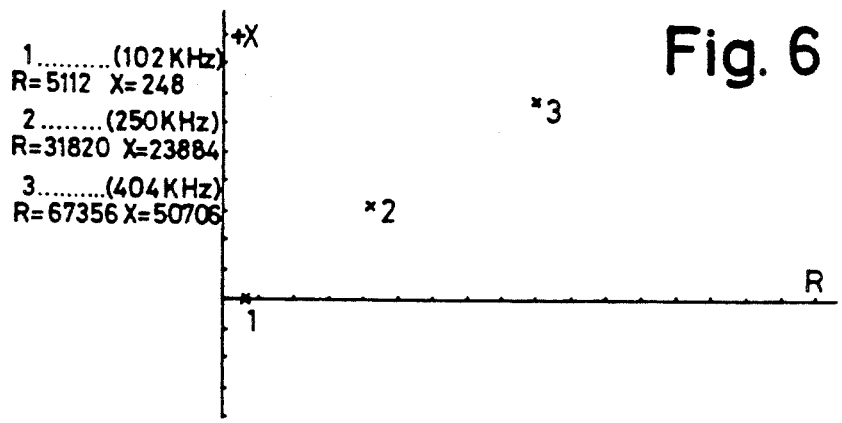
Figure 7:
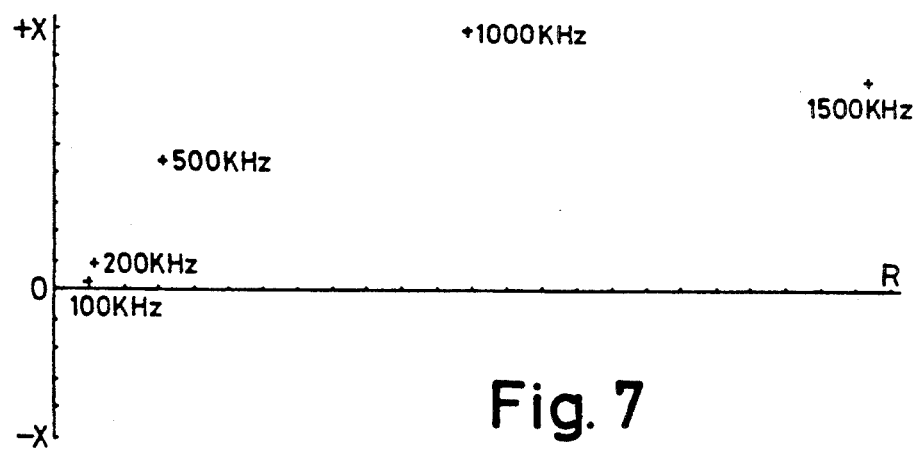
Figure 8:
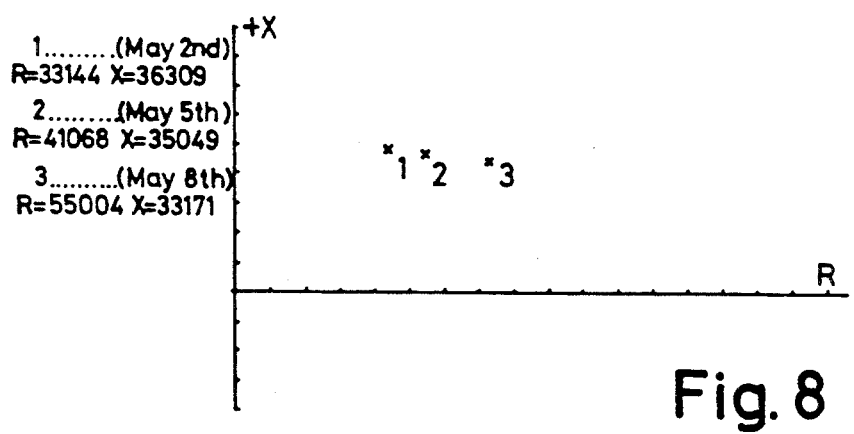

Embodiments of the invention will now be described with reference to the accompanying schematic Drawings, in which:

FIG. 1 schematically represents coils in a detector head in accordance with the invention, and used for generating an axial field, FIG. 2 is a flow diagram, FIG. 3 is a graph in which the reactive and resistive components for different materials are mapped onto an Argand diagram, FIG. 4 is an equivalent circuit for modelling capacitance and resistance of vegetable matter, such as a potato or an avocado pear, FIG. 5 is a graph illustrating the variation of the reactive and resistive components with size for different foods, FIG. 6 is a graph showing the measured reactive and resistive components for an avocado pear of the same size, the components being mapped for different frequencies, FIG. 7 is a similar graph showing a computer prediction for a potato modelled on the equivalent circuit of FIG. 5 at various frequencies, FIG. 8 is a graph showing changes in the reactive and resistive components of an avocado pear over a time span during which the pear ripened, FIG. 9 illustrates an alternative detector head with a different coil configuration for generating a vertical field, and FIG. 10 illustrates a further detector head with a different coil configuration where the sensing coil is perpendicular to the primary coil.

Referring to FIG. 1, a transmitter coil 1 is connected to an r.f. source 2 capable of generating selected frequencies from a range of high frequencies. The primary coil is supplied with a selected frequency and it thereby generates a periodically varying electromagnetic field. The frequencies used are typically within the range of 50 KHz to 500 KHz (but they could be higher for smaller items). A secondary or receiver coil 3 is placed in the vicinity of coil 1 and both coils 1 and 3 encompass an area through which a material can pass for detection. Another secondary coil 4 is schematically represented as having twice the number of turns (which are more closely spaced) and approximately one fifth the area of coil 3. Moreover, it does not encompass the area through which the material can pass for sensing. Coil 3, through which the material passes, is spaced further from coil 1 than coil 4 (e.g. if 'd' separates coil 1 from coil 4, then approximately 2d separates coils 1 and 3). This coil arrangement is such that each of coils 3 and 4 has the same inductance and picks up the same induced voltage. However, they are oppositely wound and hence these voltages cancel one another. Therefore, when a comparatively conductive material is passed through coils 1 and 3, eddy currents are set up in the material and these will effect the coupling between coils 1 and 3 only thereby causing a signal to be generated in coil 3.

Such a coil arrangement can be used to detect a complex impedance signal from non-magnetic material passing through coils 1 and 3 in the direction of the arrow showing material flow. The material may be in the form of a package or an item of fruit or vegetables, or it may be continuous, like a sausage. With individual items, the internal dimensions of the coils 1 and 3 and the distance between coils 3 and 4 preferably accommodate the item (and e.g. a conveyor belt) and these dimensions are not grossly larger than the size of the item. Otherwise, a very small item passing through the coil system would require higher frequencies to produce a useful sensing signal and this would reduce the reactive component compared with the resistive component. In the case of continuous non-metallic material, there will be a change in coupling as the front of the material enters the coil system and the signal will then remain steady whilst the bulk of material passes through the coil system until the end of the material is reached, when a further change of coupling occurs. For this reason, it is better to use the coil system described below with reference to FIG. 11.

Although some natural foods have a very low conductivity (compared with metals), if they have a comparatively large cross-section then the voltages induced will be considerable, especially near the surface where maximum flux is enclosed thereby causing sufficient eddy-current flow, with an appropriate frequency and sufficient field intensity, to provide a signal which can be detected by the sensing coil 3.

In FIG. 1, coil 4 balances the secondary coil system so that the detection sensitivity is increased for detecting the signal due to the eddy-current flow. The sensitivity enables small changes in the reactive component of the sensed signal to be detected. As changes occur in most foods (e.g. due to deterioration, drying, etc.) from the surface inwards, these changes affect the resistive and reactive components and they can be advantageously detected by the coil system.

The signal generated in coil 3 will be partly resistive and partly reactive. These components can be measured by using two separate phase detectors 5, 6. These are preferably operated in quadrature and they are adjusted so as to respond to the respective resistive and reactive components of the sensed voltage. This adjustment may be carried out by calibrating the phase detectors by 'sending' a ferrite article through coils 1 and 3 in to generate a substantially reactive component (at 90°) and then sending a piece of resistive film through coils 1 and 3 to generate a substantially resistive component (at 0°). This enables the axes of the phase detectors to be adjusted to 0° and 90° before the apparatus is used to sense food.

The resistive and reactive components of the sensed signal will reach peak values during passage of a non-magnetic material through the coil system and known digital techniques, employing an algorithm, are used for obtaining pairs of peak values of R and X from a stream of values sampled during each passage. The algorithm will also determine the sign of X. The microprocessor then compares digitised pairs of peak values with stored data which represents acceptable or non-acceptable values. This stored data may be in the form of a table of pairs of predetermined digital values of R and X.

Alternatively, the digitised peak values of R and X are applied to an equation (1) below, from which a value $K_r$ is determined to take account of different cross-sections of the non-magnetic material passing through the coil system. Thus, it can then be determined whether $K_r$ is within the acceptable range defined by $K_{low} \leq K_r \leq K_{high}$ as shown in the flow diagram of FIG. 2. In graphical terms, the optimum value of $K_r$ corresponds with the curves shown in FIG. 5 depending on the value of $\alpha$. The limits of acceptable $K_{low}$ and $K_{high}$ would be similar curves (or straight lines) passing through the origin and extending on each side of the curves shown in FIG. 5. As long as the computed value $K_r$ lies within the envelope of $K_{low}$ and $K_{high}$, the material would be acceptable. Data is stored in the memory 9b for use by the microprocessor 9a in order to make the required comparisons between measured values and predetermined stored values. The stored values can be obtained by passing known "good" samples through the coil system during a calibration procedure and storing them in the form of a table, or an algorithm can be used which computes values of $\alpha$ and $K_r$ that best fit the measured values.

By using two or more frequencies, the digitised peak values of R and X can be related to frequency so that frequency is taken into account in determining the nature or property of the non-magnetic material. Since the values of R and X will depend on the frequency used, it is possible to relate these parameters to an equivalent circuit (FIG. 4) and the values of C, R and r of this equivalent circuit can be computed for the sample material and comparisons can be made on this basis. In this case, C, R and r will vary within predetermined limits for acceptable/non-acceptable values.

The concept of "accepting" or "not accepting" measured values is applicable to "accepting" or "rejecting" samples transported on conveyor belts and this would be useful in certain applications, e.g. where ripened fruit is sorted into several different categories. However, "accepting" and "rejecting" applications are not always required and in some cases a continuous display of selected parameters is preferred in order to determine the quality or nature of the material under test. For example, the system may be used to determine the storage life of vegetable matter where the display of parameters will enable an estimate to be made of "sell-by" dates or these dates could be displayed in accordance with a predetermined algorithm. Alternatively, the displayed information can be used for manual feedback control, or channelled into an automatic feedback system for controlling a process such as the production of a material in continuous form where constituents of the material vary during the manufacture of a food product.

With regard to FIG. 2, it can be shown that the effect due to different cross-sections of the non-magnetic material passing through the sensing coil is substantially eliminated by processing the voltages R and X (which are the peak amplitudes of the reactive and resistive components from the phase detectors) in accordance with the expression:

$$K_r = \frac{X}{R^a} \quad (1)$$

where $K_r$ is a computed amplitude and $\alpha$ is a power depending on the geometry of the material (i.e. its cross-section) relative to the coils 1 and 2. Generally, for non-metallic and low conductive materials with variable cross-sections, $\alpha$ tends to be 0.5.

In the case of fruit and vegetables which have a cellular structure there is a near-linear relationship between R and X (see FIG. 5) so that the value of $\alpha = 1$ is preferred in the quadrant defined by positive reactance and positive resistance.

Therefore, to cover all possible food produce and food products $0.5 \leq \alpha \leq 1.0$.

The value of $K_r$ generally represents a size-independent parameter which characterises a particular material and is substantially unaffected by its size, orientation or cross-section (as seen by the sensing head).

Optimum expressions may be derived which give the best results with products of different shapes or compositions, e.g. approximating spheres, or having a non-uniform conductivity. The size of the material relative to the coil spacing will also affect the value of $\alpha$.

Instead of applying the values R and X to a predetermined expression, the optimum relationship between these values may be determined by trial and error. For example, a range of test samples with the same known conductivity and different known cross-section could be passed through the detection zone and the resultant values R and X stored in memory. The relationship between R, X and cross-section could then be graphically displayed as a curve (or straight line) on a screen so that an estimate could be made of an expression which would tend to linearise the effect due to cross-section and hence determine $\alpha$. This process could be repeated to obtain the best compensating expression and the best value of $\alpha$. This value of o may be input to the microprocessor which is programmed to eliminate effects due to varying cross-section.

FIG. 5 schematically illustrates the R, X relationship for foods having different cross-sections but, in each case, constant bulk conductivities. The slightly concave curves in the negative reactance quadrant will be noted since this concavity is substantially straightened out by choosing the best value for $\alpha$ to eliminate effects of varying cross-section. Foods in the upper positive reactance quadrant e.g. cellular vegetables have $\alpha = 1$.

The theory behind these graphs is as follows:

The resistive signal component is a direct measure of the conductivity of the material. The signal produced (R) varies directly with the conductivity and with the fourth power of the diameter (or cross-section squared), i.e.

$$R = k_1 d^4 \quad (1)$$

The reactive component will be negative or positive for non-magnetic substances. In FIG. 3, for example, points 11, 19 and 20 represent respectively positive reactance values of X = +31774 for iron added cereal (R=312), X = +10453 avocado pear (R=22156) and X = +17998 potato (R=43548). Points 22-28 represent respectively negative reactance values of X = 11774 for butter (R=172), X = -12442 for margarine (R=392), X = -7666 for distilled water (R=392), X = -7498 for tap Water (R=12668), X = -17666 for lean mince (R=126268), X = -18344 for standard mince (R=14902), and X = -1703 for cheese (R=109108). Diamagnetic permeability effects will give a negative signal which is proportional to the volume occupied by the substance under test. For a long item or continuous material, the volume will be proportional to the cross-section (d squared) since the distance between the coupled coils is fixed.

Thus the reactive signal $$X = k_2 d^2 \quad (2)$$

The ratio of the reactive and resistive signals X/R is the tangent of the phase angle which clearly varies with d (size of the inspected material).

However, the size (d) can be eliminated by taking the square root of (1) and substituting for d squared in (2) giving:

$$X = k_2 \sqrt{R/k_1}$$

or $$k_2/\sqrt{k_1} = K_r = \frac{X}{\sqrt{R}} \quad (3)$$

This value $K_r$ is now independent of size but characteristic of the material under test.

For small items, if the object under test is discrete and smaller than the coil spacing (i.e. between 1, 2 and 3) the reactive signal in (2) will be proportional to the cube of d. Thus the power of U in the denominator of (3) will be $R^{\frac{2}{3}}$ instead of the square root.

This is the reason for alpha preferably varying between the limits 0.5 and 1.0.

As mentioned above, fruit and vegetables exhibit a positive reactive effect. They can also be modelled by an equivalent circuit, as shown in FIG. 4, which includes a capacitance C in parallel with a leakage resistance r, the parallel connection being in series with a resistance R. In the case of a potato, using values of R=1000 ohms, r=$\alpha$ and C=1000 pF, a vector plot of the C-R model over a frequency range of from 100 KHZ to 1500 KHZ produces the plot shown in FIG. 7. Over the lower frequencies, this shows a close agreement with actual measurements on a potato sample (higher frequencies are not used in practice because the reactive component decreases with increasing frequency). Moreover, at the lower frequencies, the shape of the curve is similar for an avocado pear where, for example, FIG. 6 illustrates R and X values actually measured. The values can be modelled onto an equivalent circuit (FIG. 4) with values for R=600 ohms, r=5000 ohms and C=500 pF.

It will be noted from these Figures that a frequency range of from 50-500 KHZ is preferred for vegetable measurements. Below 50 KHZ, both R and X are too small to be usable. FIG. 7 shows that, the resistive signal increases above 1 MHZ, but the reactive signal decreases to zero.

The capacitance C is thought to arise at the cell boundaries of vegetable material where thin membrane walls separate adjacent areas of conductive fluid. Thus as the material deteriorates, the cell boundaries break down causing a increase in the resistive component and an decrease in the reactive component of the sensed signal. This occurs also when some vegetable materials have been frozen or subject to intense cold and hence the invention can detect this in such materials. In any event, measurements at two or more frequencies provide values for the equivalent circuit parameters C, R and r from which a parameter set can be derived to describe, more completely, a characteristic of the material. Digital values representing the frequencies used are stored in memory $9a$ for use by the microprocessor $9b$ together with R and X values in order to determine C, R and v.

Measurements using the above technique will be affected by temperature, since the electrical conductivity in most materials is temperature dependent. However, by sensing the temperature of the material by separate means, correction or compensation can be applied to obtain parameter sets which are temperature independent. As shown in FIG. 1, a radiation temperature sensor 21 detects temperature of the sample surface in the coil system 1 and 3. The temperature values are converted into digital form by an A/D converter 22 which supplies an input to the microprocessor $9b$. The microprocessor is also programmed with a suitable algorithm to applying compensation to the peak R and X values so that they are independent of temperature.

Whilst the coil arrangement shown in FIG. 1 can be used for most applications, it produces an axial field and hence the signal induced in the sensing coil 3 will be affected by changes in the cross-sectional area of the sample passing through the coil system. This effect can to some extent be reduced by generating a vertical field with the coil arrangement shown in FIG. 9.

In FIG. 9, a transmitter coil 1 is connected to an rf source (not shown) to generate the time-varying electromagnetic field at the required frequency. A secondary or receiver coil 3, wound parallel to coil 1, is spaced apart from coil 1 so as to define a gap through which the non-magnetic material passes, e.g. on a conveyor belt (not shown). Another secondary coil 4, similar to coil 3 but having opposite windings is also spaced from coil 1 by the same spacing as between coils 1 and 3. The windings of coil 4 are also parallel to coil 1. Coil 4 does not take part in the sensing of a signal induced in a sample passing through the gap between coils 1 and 3. However, equal and opposite voltages are induced in coils 3 and 4, whereby the induced voltage in coil 3, due to the field only, is offset by an equal and opposite voltage induced in coil 4. Coil 3 is therefore sensitive to changes in coupling due to the passage of a sample through the coil system. Apart from these differences, the apparatus is generally similar to that shown in FIG. 1.

As the coil arrangement shown in FIG. 9 generates a vertical field, the signal induced in coil 2, due to the passage of a non-magnetic material of a given "height", i.e. measured in the vertical direction of the field, will be substantially insensitive to changes in cross-section. This is more easily understood with regard to placing individual bananas on a conveyor belt passing through the coil system, the bananas being similar in size but, due to random placing, arriving at the coil system with different orientations. For example, some bananas may arrive more transverse than axial to the direction of motion. Such changes in cross-section do not produce a significant change in the signal induced in the sensing coil. However, if the "height" of the material varies, e.g. if thinner and thicker bananas were passed through the coil assembly, then variations in cross-section, due to these height changes, would need to be compensated by the method described above relating the value $K_r$ with the reactive and resistive components.

The coil system shown in FIG. 9 may also be considered to exploit the generation of eddy-currents in view of the direction of the field. This therefore promotes the reactive and resistive components which are usefully employed in accordance with the invention.

In the case of bananas, samples can be measured to determine when they are ready to pick. This is particularly useful, since it is important to pick bananas at the correct stage of maturity so that they do not arrive in shops as either unripe or over-ripe.

The coil arrangement of FIG. 9 is also preferable when making measurements on thin material such as sliced meat or meat products or thin foods such as hamburgers.

A further coil arrangement is shown in FIG. 10. In this case, a transmitter coil 1 shown in cross-section, has its windings in a plane which is perpendicular to the plane of the windings of a receiver coil 3, also shown in cross-section. Therefore, no "balance coil" is required, because coils and 3 are at right angles and have no coupling in the absence of a non-magnetic material sample. This arrangement is particularly suitable for monitoring non-magnetic material flowing in a pipeline and the cross-section of such a pipeline P is shown in FIG. 10.

With regard to various applications of the invention, it could be applied to determine the temperature of a material where its conductivity changes with temperature.

I claim:
1. A method of determining the nature or property of a non-metallic material comprising the steps of:
 a) generating a time-varying electromagnetic field in a primary coil,
 b) providing a sensing coil in the vicinity of the electromagnetic field,
 c) introducing the non-magnetic material into field whereby a signal is developed in the sensing coil, and
 d) detecting the signal developed in the sensing coil and using it to determine the nature or property of said material,
the method being characterised by:
 e) using a frequency for generating said field which will provide a distinguishable change in the reactive component in the signal induced in the sensing coil due to the presence of said material in said electromagnetic field,
 f) obviating any substantial voltage induced in the sensing coil due to said electromagnetic field alone, thereby to improve the sensitivity of the system for detecting said change in the reactive component, g) determining resistive and reactive components of the signal induced in the sensing coil due to the complex impedance of the material as the material is passed through said field, h) using said components of the complex impedance to determine the nature or a property of the non-metallic material.

2. A method according to claim 1 wherein a substantial voltage which may be induced in the sensing coil due to said field alone is obviated by arranging the sensing coil with the plane of its windings perpendicular to the plane of the windings of the primary coil.

3. A method according to claim 1 wherein a substantial voltage induced in the sensing coil due to said field alone is obviated by generating an opposite voltage in a further coil connected to said sensing coil, said further coil cooperating with the primary coil to generate said opposite voltage but not forming part of a path through the coil system and along which the non-magnetic material is passed in order to generate the complex impedance signal in the sensing coil.

4. A method according to claim 3 wherein said resistive and reactive components are quadrature components which are either purely reactive and resistive, or combinations thereof from which the purely reactive and resistive components can be computed.

5. A method according to claim 4 and further including the step of processing the reactive and resistive components in order to compute a value which is substantially unaffected by changes in the cross-section of the material passing through said field.

6. A method according to claim 5 wherein the purely reactive and resistive components are processed in accordance with the expression:

$$K_r = \frac{X}{R^\alpha}$$

where R is the amplitude of the resistive component of the sensed signal, X is the amplitude of the reactive component of the sensed signal, $\alpha$ is a power which is normally such that $0.5 \leq \alpha \leq 1.0$ (depending on the geometry of the material relative to the coil, i.e. its shape and orientation), and $K_r$ is an amplitude which is computed, and which varies in accordance with changes in the conductivity of the material but is substantially independent of the cross-section of the material passing through the field in the detection zone.

7. A method according to claim 6 wherein said field is generated by using two or more different frequencies in order to derive sets of reactive and resistive components which are characteristic of said non-magnetic material.

8. A method according to claim 7 wherein said set of values are used to determine capacitance and resistance values in an equivalent circuit for modelling the complex impedance of the non-magnetic material.

9. A method according to claim 8 wherein said reactance and resistive components or values derived therefrom are compared with a range of values which represent acceptable or non-acceptable qualities of the non-magnetic material and wherein the comparison is used for the purposes of assessing quality, or process control.

10. A method according to claim 9 wherein values representing the reactive and resistive components of different non-magnetic materials are stored and wherein sensed reactive and resistive components are compared with the stored values to determine an acceptable or nearest match to enable the sensed components to be identified as the nature or property of the non-magnetic material.

11. A method for determining the freshness or maturity of a food in which an eddy-current can be induced, or which possesses permittivity or diamagnetic properties, the method including the steps of:

(a) providing model values of complex impedance representing changes in the food with time, (b) generating an hf field with a frequency which produces a distinguishable change in the reactive component of voltage induced in the food when passed through said field, (c) obviating any substantial voltage induced in a sensing coil
due to said field only, which sensing coil is used to detect said reactive component and a resistive component, (d) measuring both the reactive components induced in the sensing coil due to the complex impedance of the food, and (e) correlating said components with said model values in order to provide an optimum correlation which is used to determine the freshness or maturity of the food.

12. A method according to claim 11 in which the food is vegetable matter wherein the resistive and reactive components are related to a degree of decay or putrefaction of said matter, the method being applied to determine the freshness or storage life of said vegetable matter.

13. A method according to claim 11 in which the food is an air-dried meat product and wherein the resistive component is related to its degree of air dried maturity.

14. Apparatus for determining the nature of a property of a non-metallic conductive material, the apparatus comprising:

a) means for passing said non-metallic material along a predetermined transport path;

b) a sensing head including:

(i) first coil means for generating a time-varying electromagnetic field, (ii) second coil means adjacent said first coil means and in which a voltage is induced due to said field only, said first and second coil means both encompassing said transport path, and (iii) third coil means adjacent said first coil means but not encompassing said transport path, said third coil means being dimensioned so that an opposite voltage is induced therein with respect to said second coil means, said opposite voltage substantially offsetting the voltage induced in said second coil means, c) means for energizing said first coil means with a frequency for generating said field, said frequency being such as to provide a distinguishable change in the reactive component of a signal induced in said second coil means due to the passage of said material through said electromagnetic field;

d) means for sensing said signal induced in said second coil means and for determining the signal induced in said second coil means, which resistive and reactive components define the complex impedance of said material; and e) means responsive to said resistive and reactive components for determining the nature of a property of said material.

15. Apparatus according to claim 14 wherein said first, second and third coil means are wound in parallel planes.

16. Apparatus according to claim 15 wherein said means (d) are separate phase detectors, operating at a relative phase difference of 90°, for detecting said resistive and reactive components.

17. Apparatus according to claim 14 including means for converting the resistive and reactive components into digital values, and means for comparing said digital values with a range of digital values which represent acceptable or non-acceptable qualities of said material.

18. Apparatus according to any of claims 14 wherein said means for energising said first coil means generates selected frequencies and wherein said means responsive to said resistive and reactive components includes processing means provided with a memory for storing values representing said components together with frequency information so as to define a characteristic for identifying the nature or property of said material.

19. Apparatus according to claim 14 in which means are provided for processing the reactive and resistive components and for computing a value which is substantially independent of the cross-section of said material passing through said field.

20. Apparatus according to claim 15 wherein the processing means are programmed to manipulate digital values representing the reactive and resistive components in accordance with:

$$K_r = \frac{X}{R^a}$$

where R is the amplitude of the resistive component of the sensed signal, X is the amplitude of the reactive component of the sensed signal $a$ is a power which is normally such that $0.5 \leq a \leq 1.0$ (depending on the geometry of the material relative to the coil, i.e. its shape and orientation), and $K_r$ is an amplitude which is computed and which varies in accordance with changes in the conductivity of the material but is substantially independent of the cross-section of the material passing through said field.

21. A method of determining the nature or property of a non-metallic conductive material comprising the steps of:
   a) generating a time-varying electromagnetic field in a primary coil,
   b) providing a sensing coil in the vicinity of the electromagnetic field,
   c) introducing the non-magnetic material into said field whereby a signal is developed in the sensing coil;
   d) detecting the signal developed in the sensing coil and using it to determine the nature or property of said material,
   e) using a frequency for generating said field which will provide a distinguishable change in the reactive component in the signal induced in the sensing coil due to the presence of said material in said electromagnetic field;
   f) obviating any substantial voltage induced in the sensing coil due to said electromagnetic field alone, thereby to improve the sensitivity of the system for detecting said change in the reactive component, said voltage being obviated by generating an opposite voltage in a further coil connected to said sensing coil, said further coil cooperating with the primary coil to generate said opposite voltage but not forming part of a path through the coil system and along which the non-magnetic material is passed in order to generate the complex impedance signal in the sensing coil;
   g) determining resistive and reactive components of the signal induced in the sensing coil due to the complex impedance of the material as the material is passed through said field; and
   h) using said components of the complex impedance to determine the nature or a property of the non-metallic material.

* * * * *

UNITED STATES PATENT AND TRADEMARK OFFICE
CERTIFICATE OF CORRECTION

PATENT NO. : 5,189,366                  Page 1 of 2

DATED : February 23, 1993

INVENTOR(S) : Geoffrey Mayo

It is certified that error appears in the above-identified patent and that said Letters Patent is hereby corrected as shown below:

Column 2, line 12, "si" should be --is--;

Column 11, line 54, "o" should be --$\alpha$--;

Column 12, line 12, "X=11774" should be --X=-11174--;

Column 12, line 15, "Water" should be --water--;

Column 12, line 59, "r=$\alpha$" should be --r=$\infty$--;

Column 14, line 37, "coils and" should be --coils 1 and--;

Column 14, line 55, "non-magnetic" should be --non-metallic--;

Column 17, line 2, "of" should be --or--;

UNITED STATES PATENT AND TRADEMARK OFFICE
CERTIFICATE OF CORRECTION

PATENT NO. : 5,189,366

DATED : February 23, 1993

INVENTOR(S) : Geoffrey Mayo

It is certified that error appears in the above-indentified patent and that said Letters Patent is hereby corrected as shown below:

Column 17, line 39, insert a comma(,) after "signal".

Signed and Sealed this

Twenty-fifth Day of January, 1994

BRUCE LEHMAN

*Attest:*

*Attesting Officer*     *Commissioner of Patents and Trademarks*

UNITED STATES PATENT AND TRADEMARK OFFICE
CERTIFICATE OF CORRECTION

PATENT NO. : 5,189,366
DATED : February 23, 1993
INVENTOR(S) : Geoffrey Mayo

It is certified that error appears in the above-indentified patent and that said Letters Patent is hereby corrected as shown below:

On the title page, item (56) insert the following:

Foreign Patent Documents

| | | |
|---|---|---|
| 528,607 | 10/1980 | Australia |
| 337,783 | 10/1989 | European |
| 353,035 | 11/1990 | European |
| 2,158,240 | 11/1985 | Great Britain |

Signed and Sealed this

Fifteenth Day of March, 1994

Attest:

BRUCE LEHMAN

Attesting Officer

Commissioner of Patents and Trademarks